United States Patent [19]
Vijg et al.

[11] Patent Number: 5,817,290
[45] Date of Patent: Oct. 6, 1998

[54] METHOD OF AND TEST KIT FOR MUTAGENESIS TESTING

[75] Inventors: Jan Vijg, Newton; Michael E. T. I. Boerrigter, Gloucester, both of Mass.

[73] Assignee: Beth Israel Deaconess Medical Center, Boston, Mass.

[21] Appl. No.: 686,954

[22] Filed: Jul. 25, 1996

Related U.S. Application Data

[60] Provisional application No. 60/001,974 Jul. 28, 1995.

[51] Int. Cl.[6] .................................................. A61K 49/00
[52] U.S. Cl. ................................ 424/9.2; 435/6; 435/29; 435/172.3; 435/325; 435/352; 435/353; 435/354
[58] Field of Search ................................ 424/9.2; 435/4, 435/7.2, 6, 29, 172.1, 325, 320.1, 172.3, 352, 353, 354; 800/2

[56] References Cited

U.S. PATENT DOCUMENTS

| | | | |
|---|---|---|---|
| 4,736,866 | 4/1988 | Leder et al. | 800/2 |
| 4,873,191 | 10/1989 | Wagner et al. | 435/172.3 |
| 5,510,099 | 4/1996 | Short et al. | 424/9.2 |
| 5,602,300 | 2/1997 | Gossen et al. | 800/2 |

FOREIGN PATENT DOCUMENTS

WO 92/17605  10/1992  WIPO.

OTHER PUBLICATIONS

Adhya, S.L. and J.A. Shapiro "The Galactose Operon of *E. Coli* K–12. I. Structural and Pleiotropic Mutations of the Operon" *Genetics* 62:231–247 (Jun. 1969).

Albertini, R.J. et al. "In Vivo Somatic Mutations in Humans: Measurement and Analysis" *Annu. Rev. Genet.* 24:305–326 (1990).

Boerrigter, M.E.T.I. et al. "Plasmid–based transgenic mouse model for studying in vivo mutations" *Nature* 377:657–659 (19 Oct. 1995).

Dollé, M.E.T. et al. "Evaluation of a plasmid–based transgenic mouse model for detecting in vivo mutations" *Mutagenesis* 11(1):111–118 (1996).

Douglas, G.R. et al. "Sequence spectra of spontaneous IacZ gene mutations in transgenic mouse somatic and germline tissues" *Mutagenesis* 9(5):451–458 (1994).

Gossen, J.A. and J. Vijg "*E coli* C: a convenient host strain for rescue of highly methylated DNA" *Nucleic Acids Research* 16(19):9343.

Gossen, J.A. et al. "Application of galactose–sensitive *E. coli* strains as selective hosts for LacZ⁻plasmids" *Nucleic Acids Research* 20(12):3254.

Gossen, J.A. et al. "Plasmid Rescue from Transgenic Mouse DNA Using Lacl Repressor Protein Conjugated to Magnetic Beads" *BioTechniques* 14(4):624–629 (1993).

Rüther, U. and B. Müller–Hill "Easy identification of cDNA clones" *EMBO Journal* 2(10):1791–1794 (1983).

Shibuya, T. and K. Morimoto "A review of the genotoxicity of 1–ethyl–1–nitrosourea" *Mutation Research* 297:3–38 (1993).

Suzuki, T. et al. "The concomitant detection of gene mutation and micronucleus induction by mitomycin C in vivo using lacZ transgenic mice" *Mutation Research* 285:219–224 (1993).

Tao, K.S. et al. "Comparison of somatic mutation in a transgenic vesus host locus" *Proc. Natl. Acad. Sci. USA* 90:10681–10685 (Nov. 1993).

International Search Report (PCT/US96/12171).

*Primary Examiner*—James Ketter
*Assistant Examiner*—Irem Yucel
*Attorney, Agent, or Firm*—Lahive & Cockfield, LLP; Giulio A. DeConti, Jr., Esq.; Ivana Maravic-Magovcevic

[57] ABSTRACT

A novel method and test kit for mutagenesis testing applicable to an organism or a cell.

28 Claims, 8 Drawing Sheets

METHOD OF AND TEST KIT FOR MUTAGENESIS TESTING

This application claims the benefit of a previously filed Provisional Application No. 60/001,974, filed Jul. 28, 1995, which is hereby incorporated by reference.

This invention was made with government support from the National Institute of Health (NIH grant 1PO1 AG 10829-01). Accordingly, the government retains certain rights in the invention.

BACKGROUND OF THE INVENTION

Various agents, such as radiation, synthetic chemicals and natural substances can produce mutations in DNA. When induced in the germ cells or somatic cells, such mutations change the genetic code. Changes in the genetic code of the germ cells can lead to defective genes which may be transferred to the offspring. The multitude of genetic diseases (e.g., cystic fibrosis, Duchenne muscular dystrophy) result from such mutations, which can newly occur in every generation. Changes in the genetic code of the somatic cells can give cancer and perhaps other diseases as well.

The danger that new or existing synthetic chemicals or other known agents (e.g., low levels of radon, microwaves) might be capable of inducing mutations has led to the mandatory testing of agents for their mutagenic capability. Existing tests that assess the mutagenic potential of substances or other agents focus either on alterations in the natural DNA of cultured cells or test directly for physiological and/or pathological (e.g., cancer) alterations in an animal. The use of cultured cells is not very reliable because treatment of cells in a culture medium does not mimic the reality of human exposure very well. For example, it does not allow one to test the agent for its ability to induce mutations in different organs and tissues. Moreover, to test for mutations in naturally occurring DNA (i.e., genes) is difficult (and therefore expensive) and not very reproducible.

On the other hand, to treat animals like mice with low doses of the test compound and then wait until a small percentage of the animals develops a disease (usually a tumor) is very time-consuming, requires a lot of animals and expensive professional animal pathologists to interpret the results. Clearly, there is a need for a test that allows for treatment of animals with low doses of the suspected mutagenic agent and measure mutations shortly thereafter; the method should be so sensitive that only low doses, few animals and a short time-period are sufficient to obtain a reliable result.

Between 1986 and 1988 a system was developed, which consisted of a transgenic mouse harboring a number of so-called shuttle vectors equipped with bacterial marker genes.

The vectors, termed bacteriophage lambda vectors, were integrated in a total number of 40 copies, each about 50,000 base pairs in length, in one of the chromosomes of the mouse. This was accomplished by microinjection of about 500 vector copies in a fertilized mouse egg. By a mechanism not fully understood, these copies integrate somewhere (almost always at only one site) in a chromosome. The chromosome simply breaks, a number of copies (in this case 40) integrate themselves head-to-tail in the gap, which then closes thereby making these vector copies a natural part of the mouse genome. From then on. this integrated DNA is faithfully transferred to all descendant cells, which include all bodily cells but also the germ cells. Therefore, the offspring will also have the same vector cluster at the same position in the same chromosome as the parent. The transgene cluster behaves like a natural piece of mouse DNA.

The advantage of this piece of artificial DNA, which behaves like natural DNA, is that it contains certain recognition sequences that can be used in combination with certain enzymes to cut the vectors out of the mouse DNA, wrap them in viral capsules and infect bacteria. After infection the individual vector particles can be recognized as clear spots on a gray bacterial lawn. The vector also contains the bacterial marker gene, in this case the lacZ gene encoding the β-galactosidase enzyme. The presence of this gene in an intact form can be easily recognized because it metabolizes a substrate called X-gal into a blue compound. Hence, all vector copies with an intact lacZ marker gene produce a clear spot which is blue, whereas the mutant genes show up as colorless spots.

The major limitation of a bacteriophage lambda shuttle vector system described above is that an important class of mutagens, termed clastogens, has been found to yield very low responses (Tao et al. (1993) Prod. Natl. Acad. Sci. U.S.A. 90:10681–10685) and Suzuki et al. (1993) Mutation Res., 285:219–224). Assuming that clastogens cause predominantly (large) deletions, the low response rate might be explained as being due to the difficulty of packaging lambda vectors smaller than 42 kb or larger than 52 kb. In addition, deletions extending into regions adjacent to the transgene concatemer are not detected since two intact cos-sites are required for the packaging of a single lambda vector. Other factors preventing the detection of size-changes smaller than about 5 kb, may involve the length of the tandemly integrated transgene cluster, which at a copy number of 40 per haploid genome represents a total of about two million base pairs of prokaryotic DNA. This might not be the optimal substrate for the mammalian DNA processing enzymes generating rearrangements. Indeed, the largest spontaneous deletion reported in bacteriophage lambda-based systems is only about 500 bases (Douglas et al. (1994) Mutagenesis 9:451–458).

Large structural alterations are a considerable fraction of the spontaneous mutation 35 spectrum in one of the few selectable target genes that can be analyzed in human cells, that is, the X-linked hypoxanthine phosphoribosyl transferase (HPRT) locus (Albertini et al (1990) Annu. Rev. Genet. 24:305–326). Mutations in HPRT can only be measured in cells that can still actively proliferate in vitro, such as human T lymphocytes. As a mutational target gene, HPRT may therefore not be representative for the situation in other cell types. Nevertheless, it seems likely that the mutation spectra obtained with the current bacteriophage lambda system do not reflect the true in vivo mutation spectra.

A technical problem associated with bacteriophage lambda systems is the relatively low recovery of these vectors from genomic DNA. Indeed, intactness of the genomic DNA is critical in obtaining maximum efficiencies in transgene rescue. However, in view of the large size of the bacteriophage vectors, the occurrence of large numbers of DNA breaks during DNA extraction is unavoidable, with apparent negative consequences for the rescue efficiencies.

To overcome all the restrictions associated with the current systems, a plasmid-based transgenic animal model was designed and the methodology to rescue plasmids from their integrated state into E. coli hosts was developed. The lacZ reporter transgene is part of the pUR288 plasmid, of which approximately 20 copies are integrated head to tail in one chromosomal location. By using a positive selection system, only plasmids harboring a mutant lacZ gene give rise to a colony (Gossen et al. (1992) *Nucleic Acid Res* 20:3254 and Gossen et al. (1993) *BioTechniques* 14:624–629). Although this system proved to work in principle, it could not be routinely used. Key problems appeared to be: (1) difficulties in reproducibly obtaining high yields of plasmid vector copies after magnetic separation; and (2) a usually high background mutant frequency after transforming the *E. coli* galE⁻ strain with the rescued plasmid copies. These problems were experienced by several laboratories who used the system (P. Gee, Xenometrix, Boulder, Colo. ; H. Inoue, Toyobo, Japan; H. van Steeg, Bilthoven, The Netherlands).

SUMMARY OF THE INVENTION

The present invention solves the problems described above and provides a first practical method of testing for mutagenesis, applicable to an organism or a cell, harboring a marker gene as part of a test region integrated into DNA of that organism or cell.

An object of the invention, accordingly, is to provide a new and improved method and test kit for mutagenesis testing that obviates the above described difficulties.

A further object is to provide for novel detection of mutations in marker transgenes by their efficient rescue and subsequent selection from bacterial cell transformants containing mutated copies of the transgene.

This invention pertains to methods and kits for mutagenesis testing.

Accordingly, the invention features a method of testing for mutagenesis, including:

providing an organism or a cell which includes a nucleic acid test region integrated into DNA of the organism or the cell, wherein the test region includes a binding region capable of specific binding to a capture moiety; exposing the organism or the cell to a treatment; contacting the DNA of the organism or the cell with the capture moiety and excising the test region from the DNA; and determining the presence of a mutation in the test region.

In a preferred embodiment, the excising step is performed prior to or simultaneously with the contacting step.

In another aspect, the invention features a method of testing for mutagenesis, including: providing an organism or a cell which includes a nucleic acid test region integrated into DNA of the organism or the cell, wherein the test region includes a binding region capable of specific binding to a capture moiety; exposing the organism or the cell to a treatment; excising the test region from the DNA and contacting the test region with the capture moiety, wherein the excising step and the contacting step are performed simultaneously in a reaction mixture or wherein the contacting step is performed prior to the excising step; and determining the presence of a mutation in the test region.

In a preferred embodiment, the method further includes a ligation step wherein the test region is circularized. In another preferred embodiment, the presence of the mutation is determined through a positive selection step. In yet another preferred embodiment, the test region further includes, in addition to a binding region, a marker gene.

In a preferred embodiment, the binding region includes a lac operator sequence. In another preferred embodiment, the marker gene is a LacZ gene. In yet another preferred embodiment, the capture moiety includes a magnetic bead coupled to a LacZ/LacI fusion protein. In a preferred embodiment the reaction mixture includes a binding buffer which promotes the binding of the test region to the capture moiety. In another preferred embodiment, the binding buffer includes Mg++ in the range from about 6 mM to about 12 mM. In yet another preferred embodiment, the binding buffer has a pH range of about 6.5 to about 7.5.

In a preferred embodiment, the treatment includes exposing the organism or the cell to an agent, e.g., radiation, a synthetic chemical or a natural compound.

In another aspect, the invention features a method of testing for mutagenesis, including: providing an organism or a cell which includes a vector integrated into DNA of the organism or the cell, the vector comprising a binding region which specifically binds to a capture moiety, and a marker gene the function of which can be altered by a mutation; exposing the organism or the cell to a treatment; excising the vector from said DNA in the presence of the capture moiety, wherein the excising step and a contacting step are performed simultaneously in a reaction mixture or wherein the contacting step is performed prior to the excising step, such that the excised vector is bound to the capture moiety; recovering the excised vector from the capture moiety; transforming a host cell with the vector; and determining the presence of a mutation in the marker gene by testing for an altered function of the marker gene.

In yet another aspect, the invention features a method of testing for mutagenesis, including: providing an organism or a cell which includes a vector integrated into DNA of the organism or the cell, the vector including a test region, wherein the test region includes a binding region capable of specific binding to a capture moiety; exposing the organism or the cell to a treatment; recovering the vector by excising the vector from the DNA and contacting the vector with the capture moiety; ligating the vector in the presence of ATP in the range of about 0.05 mM to about 0.2 mM, wherein co-precipitation of ATP with the vector is minimized; and determining the presence of a mutation in the test region.

In another aspect, the invention features a method of testing for mutagenesis, including: providing an organism or a cell which includes a vector integrated into DNA of the organism or the cell, the vector including a lac operator sequence and a LacZ marker gene; exposing the organism or the cell to a treatment; excising the vector from the DNA in the presence of a capture moiety, wherein the capture moiety includes a LacZ/LacI fusion protein coupled to a magnetic bead, and wherein the excising step and a contacting step are performed simultaneously in a reaction mixture or wherein the contacting step is performed prior to the excising step, such that the excised vector is bound to the capture moiety; recovering the excised vector from the capture moiety; transforming a host cell with the vector; and determining the presence of a mutation in the LacZ marker gene by testing for an altered function of the LacZ marker gene.

In another aspect, the invention features a kit for mutagenesis testing including: a nucleic acid test region capable of integration into the DNA of a cell or an organism, wherein said test region comprises a binding region capable of specific binding to a capture moiety; a capture moiety; and a binding/excision buffer which allows for excision of said test region from said DNA and a binding of said test region to said capture moiety to occur simultaneously.

In a preferred embodiment, the kit further includes a restriction endonuclease. In another preferred embodiment, the kit further includes a ligation buffer for circularization of said test region, the ligation buffer having ATP in the range of about 0.05 mM to about 0.2 mM. In yet another preferred embodiment, the kit further includes a host cell, e.g., an *E. coli* cell, e.g., an *E. coli* C (Δlac/galE⁻, or any derived strain which carries either a point mutation or a deletion in the galE gene) cell.

In a preferred embodiment, the test region further includes, in addition to a binding region, a marker gene, e.g., a LacZ gene. In another preferred embodiment, the binding/excision buffer includes Mg++ in the range of about 6 to about 12 mM. In yet another preferred embodiment, the binding buffer has a pH range of about 6.5 to about 7.5.

In a preferred embodiment, the test region is a pUR288 plasmid. In another preferred embodiment, the capture moiety is a LacI/LacZ fusion protein coupled to a magnetic bead.

For convenience, certain terms employed in the specification, examples, and appended claims are collected here.

The term "nucleic acid test region", as used herein, refers to a nucleic acid sequence that includes a binding domain and marker gene and can be used to transform a cell or an organism. As used herein, the term "binding domain", refers to a nucleic acid sequence capable of specific binding to a DNA binding protein or peptide. The test region can be contained within a DNA vector, typically a plasmid, which can be controllably integrated into and excised from a chromosome of a cell or an organism. For example, the test region can be a plasmid that contains a lac operator sequence and a LacZ marker gene. In a preferred embodiment, the test region is a pUR288 plasmid.

The term "capture moiety", as used herein, refers to a DNA binding protein or peptide coupled covalently or noncovalently to a solid support, either directly or via a specific binding substance. As used herein, the term "DNA binding protein or peptide" refers to a peptide that specifically interacts with deoxyribonucleotide strands. Those skilled in the art will recognize that, for purposes of the present invention, the DNA binding protein must bind specifically to a test region and, in a preferred embodiment, it must bind to the specific binding domain contained within the test region. The DNA binding protein can be a naturally occurring or a synthetic molecule, or a fusion protein, e.g., a LacI fusion protein, e.g., a LacI/LacZ fusion protein or a LacI/ProteinA fusion protein. In a preferred embodiment, the specific binding substance that couples the DNA binding protein to a solid support is an antibody. The solid support can be any insoluble matrix, e.g., a magnetic bead. In a preferred embodiment, the capture moiety is a LacI/LacZ fusion protein coupled via a mouse anti-β galactosidase antibody to a magnetic bead coated with sheep anti-mouse IgG.

The terms "protein", "peptide" or "polypeptide" are used herein interchangeably, and refer to a polymer in which the monomers are amino acids joined together through amide bonds.

The term "host cell" as used herein refers to a eukaryotic or prokaryotic cell or group of cells that can be or has been transformed by a test region, e.g., a vector, e.g., a pUR288 plasmid. For purposes of the present invention, a host cell is typically a bacterium such as $E$ coli, e.g., an $E.$ coli C ($\Delta$lac/galE⁻, or any derived strain which carries either a point mutation or a deletion in the galE gene) cell.

The term "organism" refers to a fish or a mammal, e.g., a non-human mammal, e.g., an animal, e.g., a rodent, e.g., a mouse or a rat, a rabbit or a guinea pig. The term "organism" is also intended to include transgenic mammals or transgenic fish, e.g., transgenic animals that have the test region incorporated into chromosomal DNA.

The term "cell" is intended to include any eukaryotic cell or any transgenic cell that has the test region incorporated into its chromosomal DNA. The term "cell" is also intended to include a plurality of cells, e.g., a cell line.

The term "treatment", as use herein, refers to an exposure of an organism or a cell to an agent to be tested for mutagenicity. The agent can be radiation, e.g., exposure to X-rays, microwaves, low levels of radon, a chemical compound or a naturally occurring compound. For example, an agent can be a mutagenic agent, e.g., a clastogen or a carcinogen.

The term "performed simultaneously", as used herein, refers to a time span in which reagents, e.g., a test region, restriction endonuclease and a capture moiety, are introduced into a reaction mixture in such a manner that an excising and a contacting step occur concurrently at least at one point in time. In a preferred embodiment, an excising and a contacting step are performed in the same reaction mixture. In another preferred embodiment, the reagents are added to the reaction mixture such that an excising and a contacting step occur concurrently for a substantial amount of time required for excision and binding to be completed.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual,* 2nd Ed., ed. by Sambrook, Fritsch and Maniatis (Cold Spring Harbor Laboratory Press: 1989); DNA Cloning, Volumes I and II (D. N. Glover ed., 1985); *Oligonucleotide Synthesis* (M. J. Gait ed., 1984); Mullis et al. U.S. Pat. No. : 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

Other features and advantages of the invention will be apparent from the following detailed description, and from the claims.

DETAILED DESCRIPTION OF THE DRAWINGS

FIG. 1 illustrates the sequence of process steps for performing the invention.

FIG. 2 illustrates the principles of the positive mutant selection system on the basis of the galactose operon of $E.$ coli. The expression of three genes (galK, galT and galE) is regulated by one operator sequence (O). One transcript gives rise to three gene products. The three enzymes catalyze a chain reaction transforming galactose into uridine diphosglucose UDPGlu), via galactose-1-phosphate (Gal-1-P) and uridine diphosphogalactose (UDPGal). After Adhya and Shapiro (1969) Genetics 62:231–247).

FIG. 3 illustrates the efficiency of rescue of the pUR288 plasmid from 50 μg total genomic spleen DNA analyzed by means of Southern blot analysis. Samples, equivalent to 2 μg total genomic DNA were taken after each step along the rescue protocol. Lanes are: (a) first supernatant obtained after magnetic separation; (b) supernatant obtained after washing lacI repressor magnetic beads; (c) supernatant obtained after incubation of lacI repressor magnetic beads with IPTG and HindIII; (d) supernatant obtained after heat inactivation of HindIII; (e) supernatant obtained after ligation and removal of the lacI repressor magnetic beads; (f) redissolved DNA pellet after ethanol precipitation; (g) HindIII digested total genomic spleen DNA.

Figure 6:
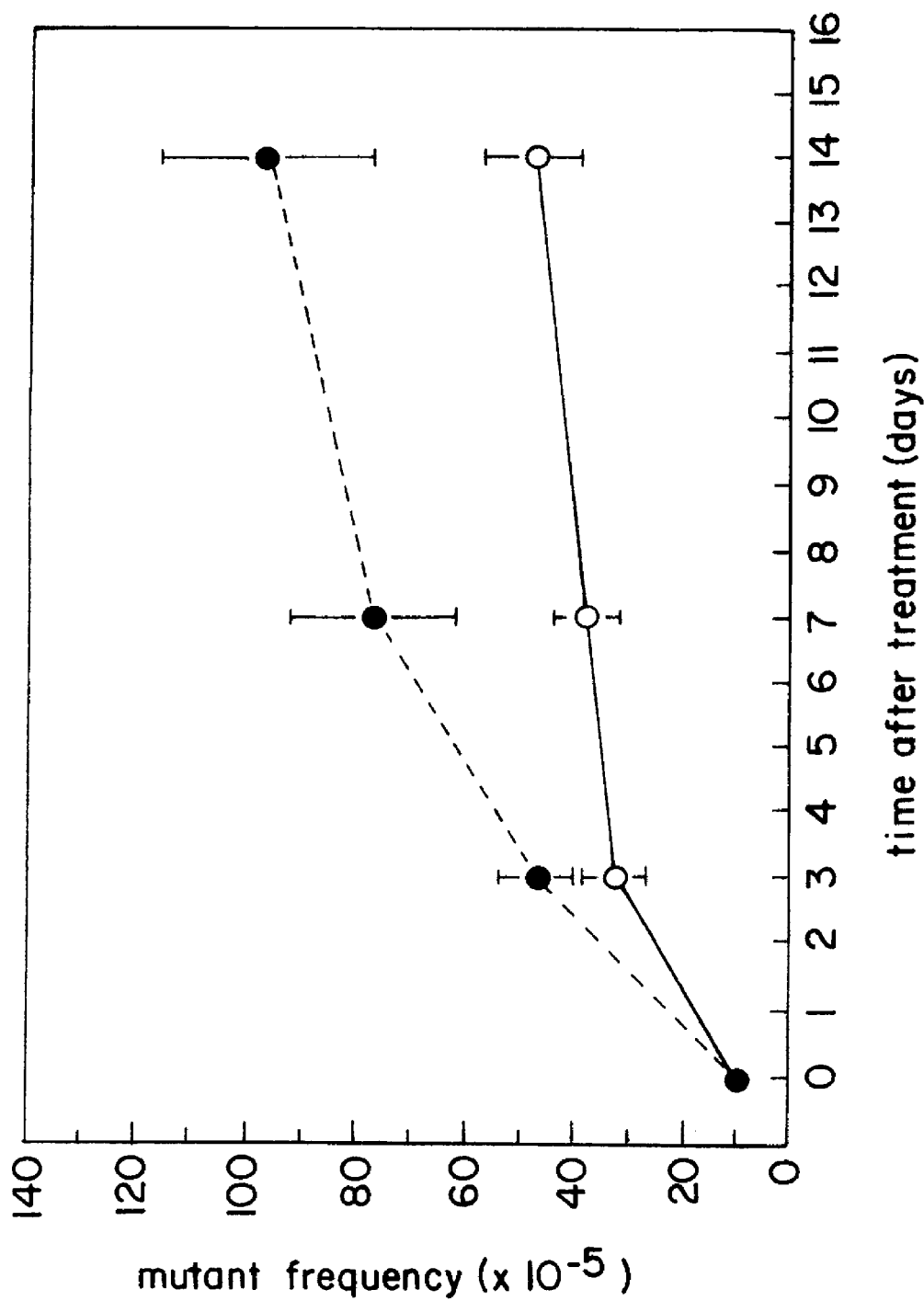

FIG. 6 illustrates the mutation induction in spleens of 6 to 8 week old pUR288 transgenic mice by ENU, administered i.p: (○) 100 mg ENU per kg bodyweight; (●) 250 mg ENU per kg bodyweight. Values were derived from 2 independent experiments, in each of which 3 animals were used per dose/time point. Error bars indicate the estimated standard deviations. Per animal between 326,000 and 11,503,000 cfu were scored.

Figure 7A:
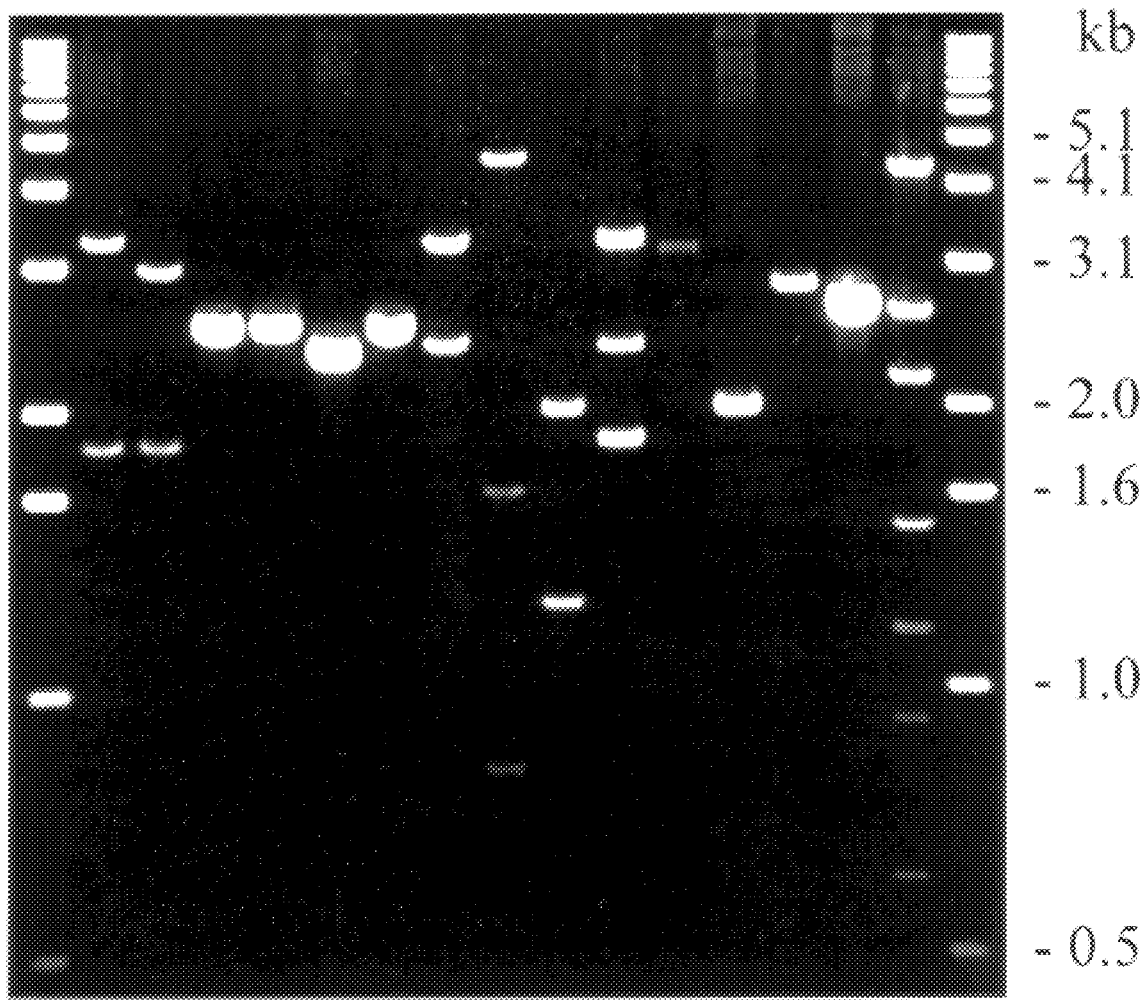
Figure 7B:
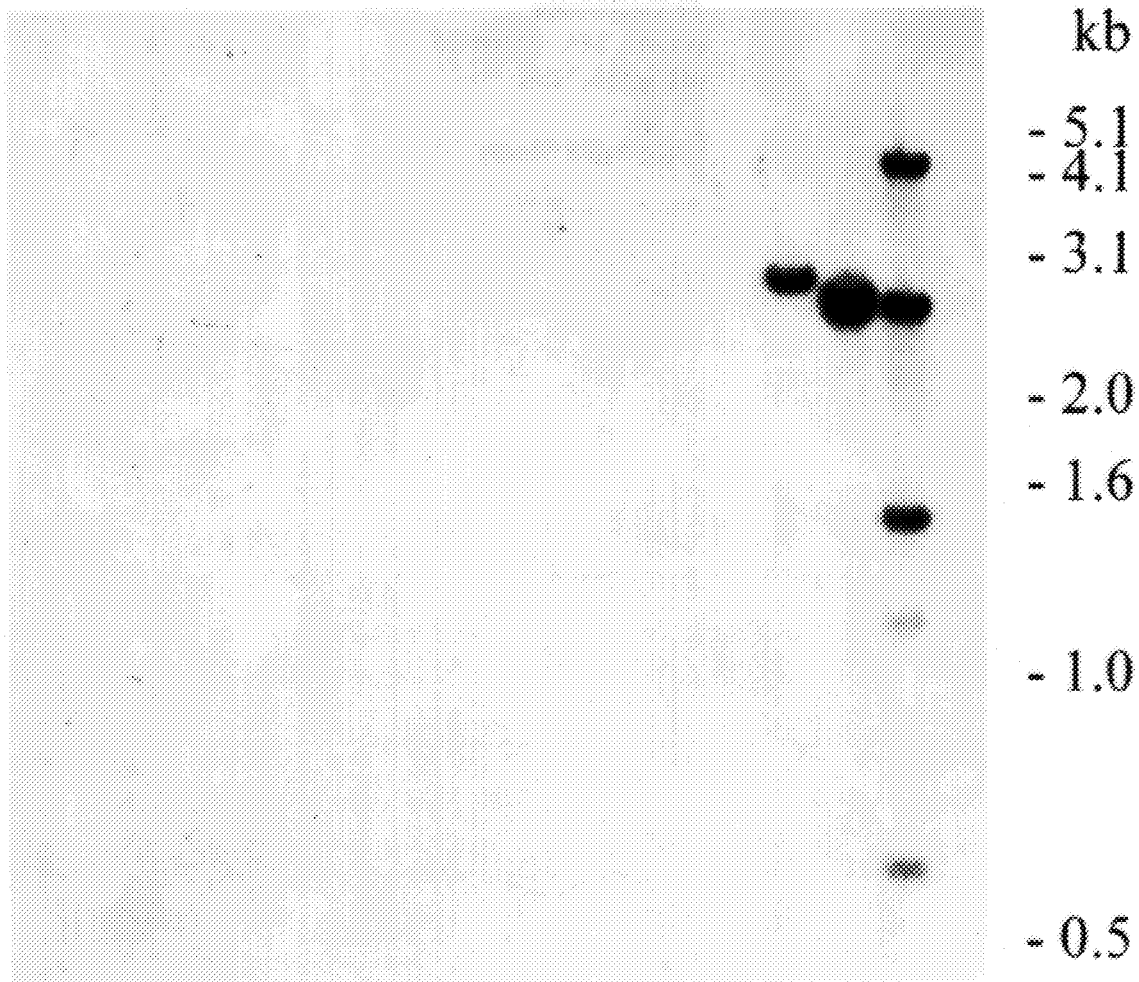

FIGS. 7A and 7B illustrates the plasmid size analysis of PstI/SacI digested pUR288 size-change mutants, isolated from spleen tissues of control and ENU treated mice. (7A) Ethidium bromide stained pattern of the selected mutants. (7B) Hybridized with $^{32}$P labeled total genomic mouse DNA. Lanes are: (a, q) 1 kb DNA ladder; (b) no-change mutant; (c–p) selection of size-change mutants.

DETAILED DESCRIPTION OF THE INVENTION

The present invention involves a routinely applicable protocol for the rescue and mutational testing of nucleic acid test regions from their integrated state in one or more of the chromosomes of an organism or a cell. Below some key aspects of this protocol are discussed.

1. DNA Extraction

With bacteriophage lambda models DNA extraction is a problem. This is due to the large size of the bacteriophage lambda vector, i.e., about 50,000 basepairs. At a total of 40 copies this means a stretch of 40×50,000=2,000,000 basepairs. During DNA extraction breaks are easily introduced and the average size of genomic DNA isolated from mammalian cells or tissues is no more than 100,000 basepairs on average. This means that many vector copies are damaged and can not be recovered unless tedious and time-consuming DNA extraction protocols are used.

Plasmids, however, are only about 5,000 basepair long. At 20 copies this means a stretch of 20×5,000 basepairs=100,000 basepairs. Naturally this poses much less of a problem. Hence, the possibility to use rapid DNA extraction protocols which are widely available on a commercial basis but could not be used for the current bacteriophage lambda models. The results presented herein show that a typical commercially available DNA extraction kit yields even better results in terms of rescue efficiency as the tedious phenol/chloroform extraction procedures used for the bacteriophage lambda models (Table 3).

2. Plasmid Purification and Rescue

Figure 1:
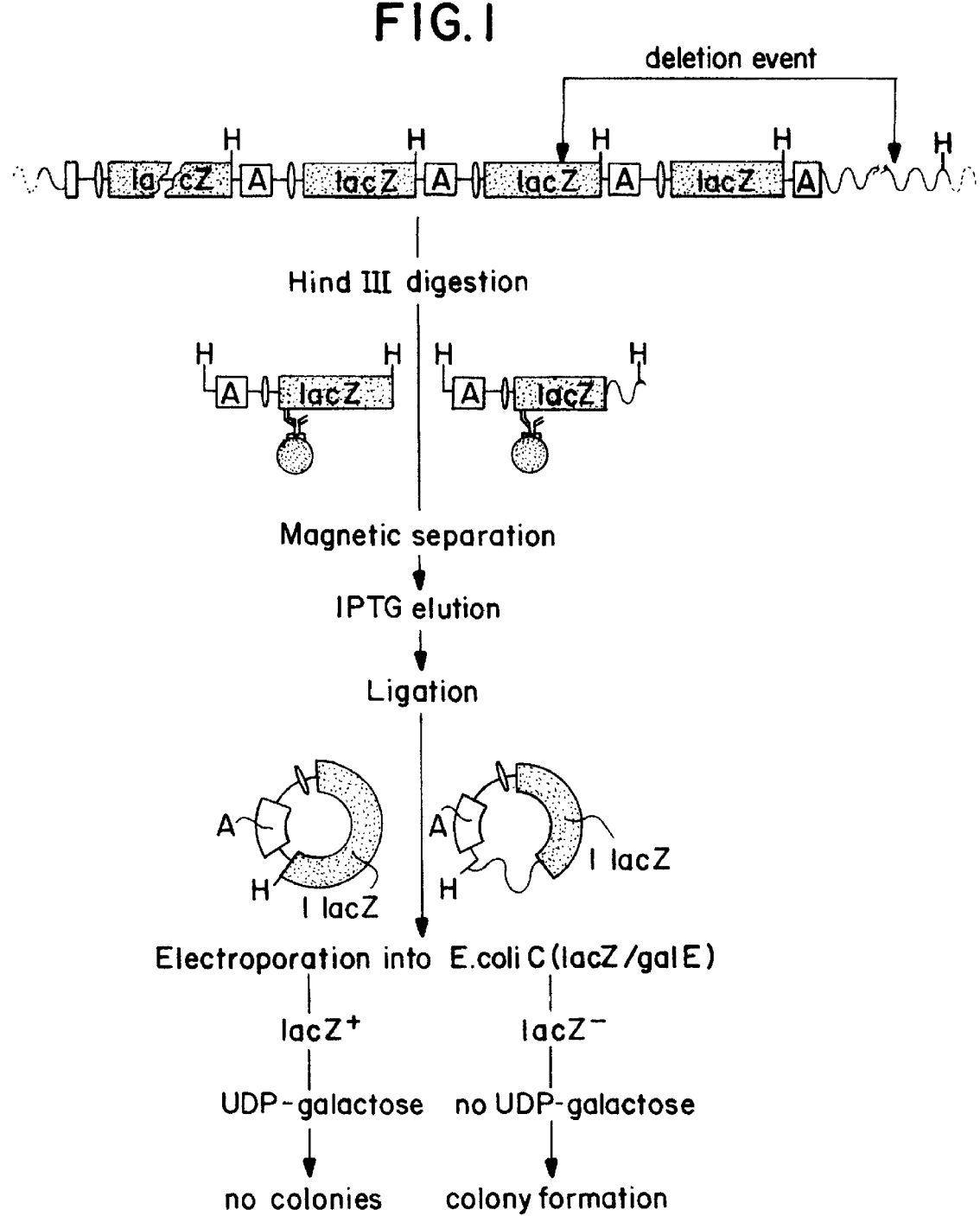

FIG. 1 illustrates the procedures used to separate the plasmids from the mouse genomic DNA after restriction enzyme digestion and to subsequently electrotransfer them into E. coli to inspect the reporter gene for mutations. Since the recovery of plasmids is not as size-dependent as bacteriophage lambda in vitro packaging, even large deletions extending into the flanking regions of the host chromosomal DNA should be detectable, provided the antibiotic resistance gene and the origin of replication are recovered. Hence, besides point mutations, all kinds of DNA rearrangements are detectable. In FIG. 1 this is illustrated by the rescue of a large deletion, extending into the 3'-flanking region of the transgene cluster. This will necessarily result in the inclusion of a mouse genomic DNA fragment in the rescued plasmid.

Plasmids containing the lacZ reporter gene are excised from the genomic DNA by incubating the genomic DNA sample simultaneously with Hind III restriction enzyme and lacI repressor proteins coupled to magnetic beads. In the current protocol this separation step is almost 100% efficient and highly reproducible. After circularization by ligation, still in the presence of the magnetic beads, the plasmids are separated from the beads, ethanol precipitated and electrotransferred into E. coli C lacZ$^-$, galE$^-$host cells. The bacteria are host-restriction negative in order to prevent degradation of incoming (methylated) plasmid DNA (Gossen and Vijg (1988) Nucl. Acids Res. 16:9343). The mutation in galE facilitates the positive selection of lacZ mutants on medium containing the lactose-analog P-gal. GalE mutants lyse in the presence of galactose because they lack the enzyme UDPgal 4-epimerase. This is apparently the result of the accumulation of UDP-galactose and the formation of defective cell walls (Adhya and Shapiro (1969) Genetics 62:231–247). Therefore, in this system the non-mutants are killed and only the lacZ cells, i.e., with (large) deletions or point mutations, can form colonies (Gossen et al. (1992) Nucleic Acid Res, 20:3254). However, in the present protocol glucose or medium components likely to contain glucose are left out of the selective medium (the medium containing the lactose analog P-gal). Indeed, in the presence of glucose non-mutants can sometimes survive by not metabolizing the P-gal thereby causing a high background.

It was found that the procedure, schematically depicted in FIG. 1, is so efficient that in one single experiment millions of plasmid copies can be recovered. Per microgram of genomic DNA between 100,000 and 200,000 transformants are routinely obtained. In practice this means that even from very small amounts of tissue a reliable estimate of the mutation frequency can still be made. With the about 10 times larger bacteriophage lambda vectors it is not possible to obtain genomic DNA large enough to even approach the efficiencies obtained with the plasmid model. Indeed, a practical advantage of the plasmid system is that rapid automatic DNA extraction procedures can be used, since the size of the extracted genomic DNA is much less of an issue (see above).

3. Mutant Frequencies and Spectra

With the protocol described above mutant frequencies were determined in different organs and tissues of untreated animals and animals treated with different mutagenic agents.

Table 4 shows that the spontaneous mutant frequency in this model is between 4 and 7×10$^{-5}$. This is higher than reported for the bacteriophage lambda models (Douglas et al. (1994) Mutagenesis 9:451–458), which could be explained by the greater sensitivity of the plasmid system for DNA rearrangement events. Indeed, in about half of the spontaneous mutants the lacZ gene appeared to have undergone size-changes, mostly deletions varying from about 50 to 3000 basepairs. As predicted and illustrated in FIG. 1, a few percent of these size changes were found to contain mouse sequences. This was indicated by a positive hybridization signal with $^{32}$P-labeled (non-transgenic) mouse genomic DNA probe (FIG. 7B). None of the mouse mutants are likely to have been generated in E. coli, which was checked by the electrotransfer and subsequent inspection for mutations of pUR288 plasmid, not prepared from the mouse, but in E. coli itself.

The capacity of the system to detect induced mutations is illustrated by an elevated mutant frequency after treatment with different known mutagenic agents. Several organs were analyzed, but in Table 1 only the results for the spleen are compared. Whole body irradiation with 5 times 50 rad resulted in an about 4-fold induction of mutations, with about the same percentage of deletion mutations as in the untreated animals. An intraperitoneal injection of 250 mg per kg bodyweight of ethyl nitrosourea (ENU) resulted in an about 10-fold induction of mutations. Interestingly, in these animals the percentage of deletion mutations was much lower; about 14%. This is easily explained by the known predominance of point mutations in the ENU mutation spectrum.

Something comparable was observed after intraperitoneal injection with 100 mg per kg bodyweight benzo[a]pyrene. This resulted in an about 4-fold induction of mutations; while in the control animals 46% were deletion mutations, in the B[a]P-treated animals this was reduced to about 30%. (B[a]P and to a lesser extent ENU are not entirely incapable of inducing DNA rearrangements as indicated by the chromosomal aberrations and micronuclei found to be induced by these compounds (Shibuya and Morimoto (1993) *Mutation Res.* 297:3–38).

were lacking suitable endogenous genes for studying mutations in animal tissues. The present model system, which is sensitive to a broad spectrum of mutations including large structural alterations, would fill in this gap in a cost-effective manner. A key issue here is whether or not a surrogate target gene provides a realistic picture of the actual situation in the genome. However, in view of the large variety in genomic environments, there is probably also no single natural gene or genomic region that reliably reflects the situation overall.

In the practical application of the plasmid model in studying somatic mutagenesis three factors are of major importance. First, the plasmid vector is much smaller than bacteriophage lambda, which greatly simplifies DNA extraction. Indeed, rapid (automated) DNA extraction procedures can easily be used and still provide very high vector rescue efficiencies. Second, the efficiency of plasmid rescue is so high that even very small amounts of tissue still allow reliable mutant frequency determinations. Third, the possibility to detect lacZ mutants by a simple selection procedure rather than on the basis of color, greatly simplifies the assay and saves time and costs.

These practical considerations in combination with its broad sensitivity to all kinds of mutational events indicates that this current model will be instrumental in obtaining insight into mechanisms of mutation induction in higher animals.

The present invention, as before stated, involves a reproducible and highly efficient protocol for the rescue of marker genes from their integrated state in mammalian chromosomal DNA followed by the positive selection of the mutants in galE$^-$E. coli cells. Before providing the detailed protocols themselves, first the different steps in the developed protocols with their efficiencies and where they differ from the original method (Gossen et al., (1993) *BioTechniques* 14:624–629) will be discussed on the hand of the results obtained.

TABLE 1

Mutant frequencies (MF) from analysis of spleen after indicated treatments

| | | | | | Mutation type (%) | | Inserted mouse sequence |
|---|---|---|---|---|---|---|---|
| Treatment | Dose | Time | MF ($\times 10^{-5}$) | n | no change | size change | (%) |
| Control | — | 14 d | 5.3 ± 0.6 | 3 | 54 | 46 | 1.9 |
| ENU | 250 mg/kg | 14 d | 97 ± 19 | 3 | 86 | 14 | 1.4 |
| X-rays | 5 × 50 rads | 10 d | 21.3 ± 2.9 | 3 | 53 | 47 | 4.7 |
| B[a]P | 100 mg/kg | 14 d | 20.1 ± 3.7 | 3 | 70 | 30 | 2.0 |

4. Applications and Practical Considerations

Efficient plasmid purification together with positive selection of mutant plasmids, make this present pUR288-C57B1/6 transgenic mouse a powerful assay to study a broad spectrum of mutations in a variety of cell types in the mouse. The model should be useful to directly study a number of hypotheses linking somatic mutations to physiological and pathological endpoints, such as cancer, aging, overnutrition. In addition, the effect of one or more inactivated genes involved in DNA damage metabolism (e.g., antioxidant defense, DNA repair) on mutation frequency and spectra can be studied directly in double transgenics, that is, in the plasmid mouse in which specific genes have been altered or inactivated.

A more practical application involves genetic toxicology testing. Strategies for evaluating mutagenic hazards in vivo A number of control experiments are also included, the results of which unequivocally demonstrate that this system is capable of detecting mutations that originated in the mouse.

A. Rescue Efficiencies

Procedures for plasmid rescue, in which the magnetic separation step was almost 100% efficient, have been described previously (Gossen et al., (1993) *BioTechniques* 14:624–629). However, these protocols appeared not to work on a reproducible basis and to suffer from a number of serious defects making them overall much less efficient. More specifically, problems were often experienced in obtaining high plasmid yields after magnetic separation and high background mutation levels due to the occurrence of false positives. Therefore, we found it necessary to work out a novel set of protocols. This turned out to involve a number of rather basic changes that we consider as both novel and unexpected for someone of moderate skill in the art.

The protocols differ from the original ones (Gossen et al., (1993) BioTechniques 14:624–629) at several points. Key factors appeared to be (1) the pH of the binding buffer (2) the addition of Mg++ to the binding buffer and (3) the exposure of the magnetic beads (coupled to the lacZ/lacI fusion protein) to the genomic DNA prior to or simultaneously with the Hind III restriction enzyme digestion. The exposure of the beads to much larger DNA fragments greatly increases the binding efficiency. This latter change also shortened and simplified the protocol. Then, elution of the plasmids from the beads (now done with both IPTG and a short heat-shock) and ligation are done in the presence of the beads in the same tube and buffer. These changes have shortened the protocol from the earlier 6 hours and 4 steps (digestion, binding, ligation and ethanol-precipitation) to 4 hours and 3 steps (digestion/binding, ligation and ethanol-precipitation).

An important fourth point of deviation from the old protocol is the ten times lower amount of ATP during ligation. It has been found that the higher amount of ATP often caused co-precipitation with the plasmids. This reduced the time-constant of electroporation and reduced the efficiency of electroporation.

Figure 2:
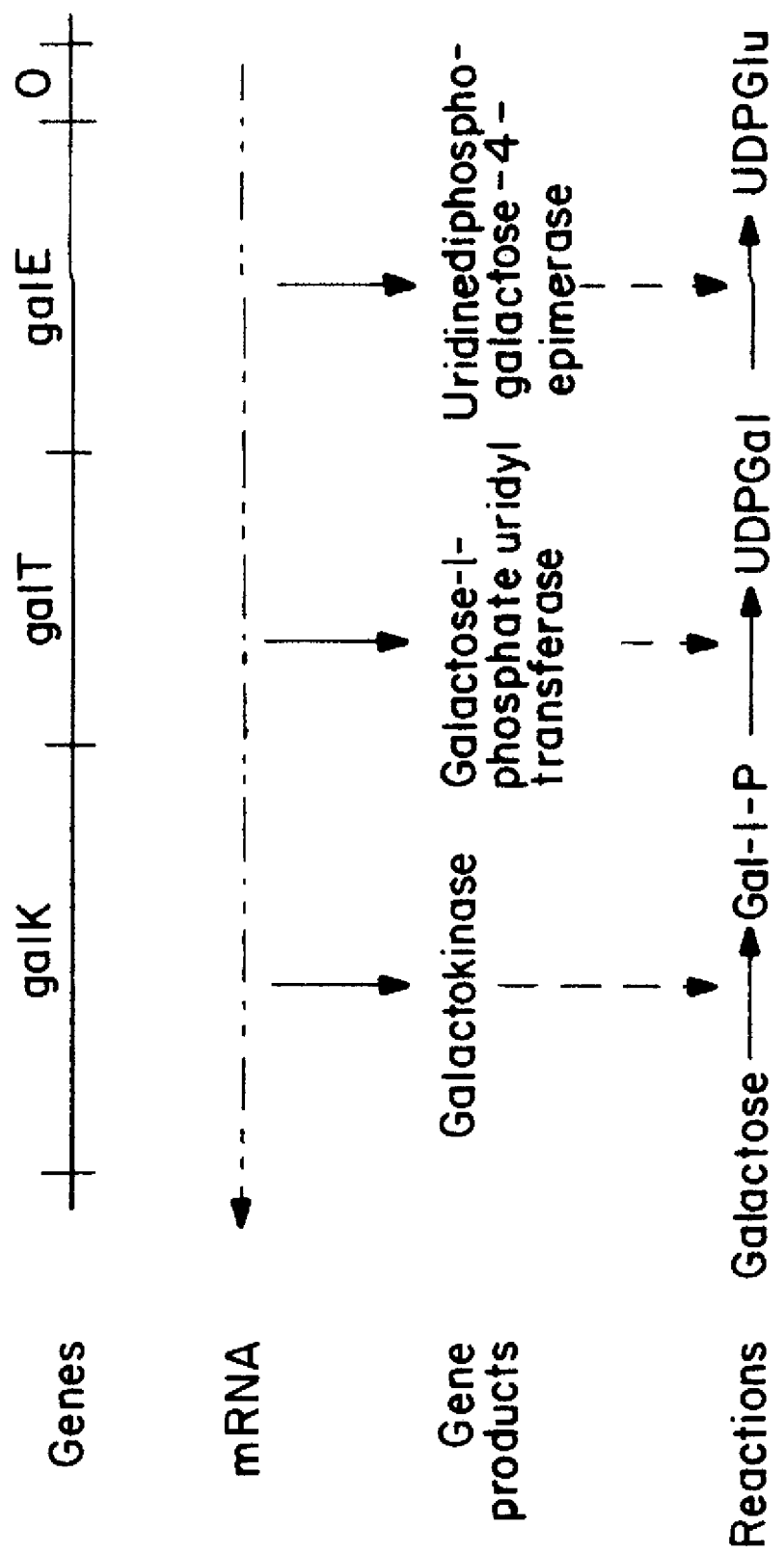

Using the modified protocol, plasmids were separated from total genomic mouse DNA with almost 100% efficiency. This was indicated by Southern hybridization experiments, using the plasmid as a probe, to monitor the relative intensities of the plasmid band in the different preparations along the rescue protocol (FIG. 2). Signal strength analysis, using a phosphorimager, of each individual band indicated that less than 4% was lost after binding to and washing of the magnetic beads (lane a and b), finally resulting in 80% ligated and precipitated plasmid sequences (lane f), as compared to the signal strength of a equivalent amount of HindIII-digested genomic DNA (lane g).

Table 2 shows the rescue efficiencies obtained with the purified plasmids after electrotransformation into $E.\ coli$ C, lacZ$^-$, galE$^-$, using two different batches of electrocompetent cells. These results indicate three possible sources of variation. The single most important variable appeared to be the transformation efficiency of the electrocompetent cells; for the same DNA samples on average 2 to 4 times more transformants were obtained with batch B than with batch A. By using commercially available pUC 19 plasmid it was established that batch B had an efficiency of $6\times10^{10}$ transformants per µg pUC 19, while the efficiency of batch A was 2.7 times less.

Second, sample to sample variation in rescue efficiency was observed, but usually much less than a factor of two. Since the size of the genomic DNA is unlikely to influence lasmid rescue efficiency, DNA sample variation could be due to variable protein and/or carbohydrate contamination which may influence the electroporation efficiency. Third, there was some influence from one experiment to the other. But this was small, even when different amounts of genomic DNA were used (Table 2).

A major conclusion that can be drawn from Table 2 is that the numbers of transformants obtained in one single experiment are high, on average, and very high occasionally. Indeed, while on average 100,000 transformants per µg genomic DNA were obtained, yields well over 100,000 were no exception.

TABLE 2

Plasmid rescue efficiencies from total genomic spleen DNAs, isolated from 8 different transgenic mice, for two different batches of electrocompetent cells.

| Sample | Electrocompetent cells - batch A[a] | | | Electrocompetent cells - batch B[a] | | |
|---|---|---|---|---|---|---|
| | µg DNA | No. of colonies × $10^3$ | cfu/µg DNA × $10^3$ | µg DNA | No. of colonies × $10^3$ | cfu/µg DNA × $10^3$ |
| 1 | 20 | 633 | 32 | 20 | 2590 | 130 |
| | | | | 14 | 1612 | 115 |
| 2 | 20 | 1370 | 69 | 10 | 2150 | 215 |
| | | | | 3 | 352 | 117 |
| 3 | 20 | 344 | 17 | 20 | 2590 | 86 |
| | | | | 14 | 924 | 66 |
| 4 | 20 | 496 | 25 | 20 | 1200 | 215 |
| | | | | 14 | 616 | 44 |
| 5 | 20 | 808 | 40 | 20 | 2940 | 147 |
| | | | | | 6 | 784 | 131 |
| 6 | 20 | 1496 | 75 | 20 | 2770 | 139 |
| 7 | 20 | 1352 | 68 | 20 | 2380 | 119 |
| 8 | 20 | 1348 | 67 | 20 | 2610 | 131 |

[a]Transformation efficiency of batch B was $6 \times 10^{10}$ transformants per µg pUC19; the transformation efficiency of batch A was 2.7 times lower.

To investigate the possibilities of using rapid DNA extraction kits instead of the tedious phenol/chloroform extraction procedures, this latter method (method 1) was compared with a commercially available DNA extraction kit: the "Tissue DNA Kit" (method 2). Both methods yielded comparable amounts of total genomic DNA from mouse livers. Possibly the average size of the DNA obtained with method 2 was much lower, but the purity seemed higher (indicated by the $OD_{260}$ $OD_{280}$ ratio, results not shown).

The mutant frequency determinations, with 30 µl genomic DNA per assay, revealed identical or almost identical values between the same liver samples, prepared with the two different methods (Table 3). Restriction analysis of the mutations revealed no major differences between the two methods with regard to the proportion of size-change mutants larger than 25 base pairs (data no shown). However, the rescue efficiency, expressed as total number of transformants per µg of DNA, was considerably higher in the samples purified with method 2. This shows that this method yields a DNA that is better suitable for immunomagnetic rescue, perhaps by a more complete removal of contaminating molecules such as proteins or lipids that could interfere with DNA binding to the beads. It is possible that other commercially available DNA purification systems work as well as the one used in this study.

The results obtained clearly indicate that rapid DNA extraction protocols, such as the commercially available kit used in this study, can be applied to in vivo mutagenicity testing using the recently developed plasmid-based transgenic mouse model. Since the average fragment size of this DNA is about 50–100 kb (Qiagen (1995) Genomic DNA handbook), it is unlikely that this kind of rapid procedure can ever be used for mutation analysis with baceriophage lambda based systems, given the requirement of high molecular weight DNA for efficient in vitro packaging.

TABLE 3

Determination of rescue parameters and LacZ mutant frequencies with genomic DNA purified with two different methods from livers of pUR288 transgenic mice (*cfu = colony forming units).

| Tissue | DNA purification method | *cfu on titer plate (× 1000) | *cfu on selective plate) | Rescue Efficiency (cfu × 1000/μg genomic DNA) | Mutant Frequency (× $10^5$) |
|---|---|---|---|---|---|
| animal 1 | method 1 | 416 | 48 | 22.7 | 11.5 |
| animal 1 | method 2 | 1220 | 140 | 28.4 | 11.5 |
| animal 2 | method 1 | 182 | 14 | 17.8 | 7.7 |
| animal 2 | method 2 | 772 | 55 | 41.5 | 7.1 |

B. Spontaneous Plasmid Mutant Frequencies in the Mouse

A key problem with the old protocol was the often high to very high numbers of colonies on the selective plates, representing false positives. In principle, no transformants should grow that contain wild-type lacZ plasmids. Indeed, the β-gal activity allows them to metabolize P-gal (the lactose analog) resulting in UDP-galactose accumulation and cell death. However, we found that even small amounts of glucose in the medium were enough to allow also a considerable number of non-mutants to grow. This, however, appeared to be unpredictable; sometimes there was a very high background, sometimes it was normal. Hence, the difficulties in standardizing the original protocol. This point five of the listed differences between this and the original protocol was enough to also get this part to work on a routinely basis. This is now illustrated on the hand of some experiments in which the spontaneous mutant frequencies in various organs of the mouse were determined.

Spontaneous mutant frequencies in various tissues of about 4-month old mice ranged from 4 to $7×10^{-5}$. Table 4 shows mutant frequencies found for spleen, kidney, liver and lung 1 5 in three untreated animals. The number of transformants screened per organ per animal ranged from 1,074,000 to 8,587,000. The experimental variation between mutant frequency determinations of the same sample ranged from 5% to 35% (coefficient of variation). No significant differences were observed between organs and between the three animals for each respective organ.

TABLE 4

Spontaneous LacZ-mutant frequencies in various organs of 4-month old transgenic mice

| Organ | No. of animals | No. of total colonies × $10^3$ | No. of mutants | Mutant frequency (mutants/total # of cfu)[a] × $10^{-5}$ SC[b] |
|---|---|---|---|---|
| Spleen | 8 | 18023 | 922 | 5.3 ± 0.4 |
| Kidney | 8 | 11798 | 681 | 5.8 ± 0.8 |
| Liver | 10 | 27098 | 1774 | 6.4 ± 0.5 |
| Lung | 8 | 9356 | 398 | 3.9 ± 0.9 |
| Brain | 8 | 30148 | 1328 | 4.4 ± 0.5 |

[a]Means are derived from individual animal mutant frequencies
[b]Standard deviation of the means

C. Mutant Frequencies in E. coli

To investigate in how far the spontaneous mutant frequency found in mouse tissues is affected by mutations occurring in E. coli, different amounts of purified pUR288 plasmids were electroporated into E. coli C (lacZ⁻/galE⁻). As shown in Table 5, the overall mutant frequency of E. coli C is (1.1 ±0.7)×$10^{-5}$ over a range of (2–16)×$10^5$ transformants plated on the selective plates.

TABLE 5

LacZ mutant frequency in E. coli

| Mutant type | No. of mutants[a] | Mutant frequency × $10^{-5}$ of SD[c] |
|---|---|---|
| total mutants | 61 | 1.05 × 0.72 |
| galE insensitive | 23 | 0.25 ± 0.39 |
| no-change | 22 | 0.58 ± 0.57 |
| size-change | 16 | 0.22 ± 0.26 |
| original size-change | 3 | 0.11 ± 0.16 |

[a]Out of total of 4.851 × $10^6$ colonies
[b]Means are derived from individual animal mutant frequencies determinations of the same sample, ranging from 209,000 to 1,616,000 transformants per plate (n = 6).
[c]Standard deviation of the mean.
[d]Total number of size-change mutants corrected for duplicate mutant plasmids found, due to clonal effects during culture growth.

Figure 3:
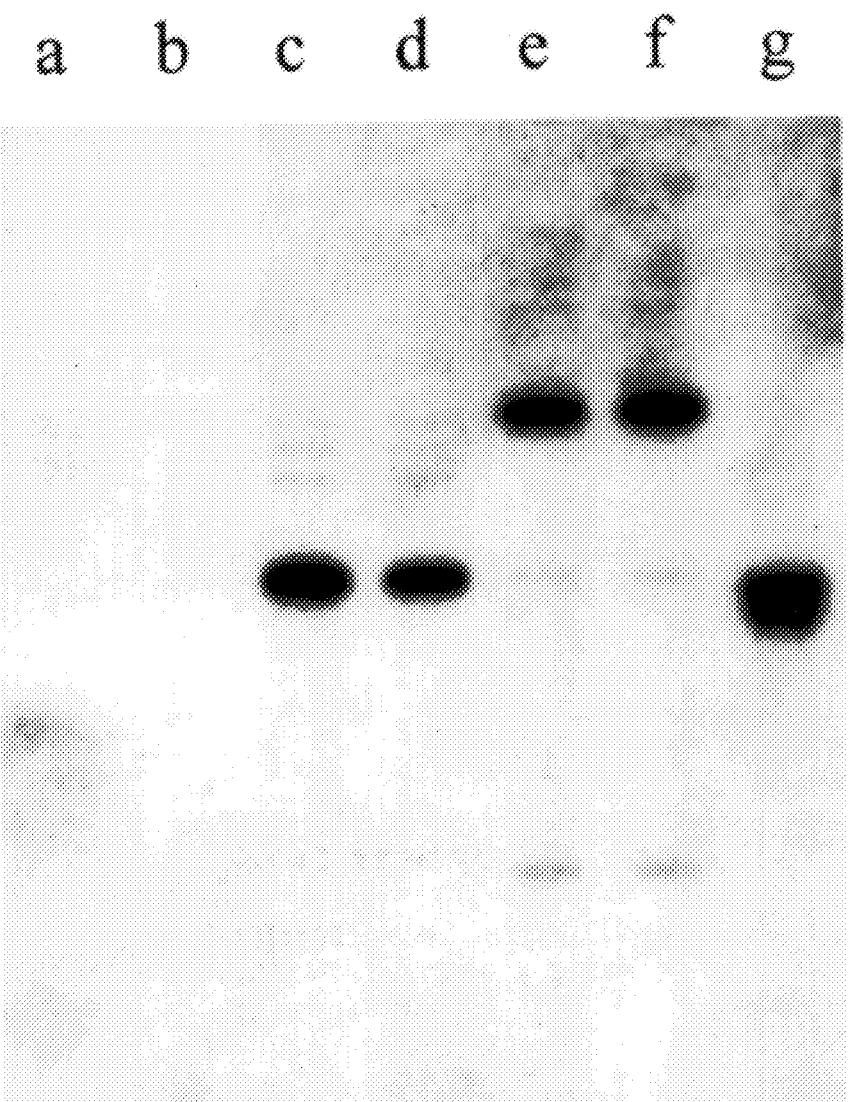

Since P-gal is converted into phenol and galactose by an intact lacZ product, and galactose is converted to UDP-galactose by the enzymes encoded by the galK and galT genes, cells will die when they are not capable of metabolizing this last toxic compound (FIG. 3). So, in principle, only E. coli cells harboring a mutated lacZ gene will be able to survive on the selective medium. However, it is possible for E. coli cells, harboring a wild type pUR288 plasmid, to grow in the presence of P-gal, when the galE gene is reverted back to wild type. Cells that have a functional galE product will convert the toxic UDP-galactose into UDP-glucose. In addition, a forward mutation in the galK or galT gene will prevent the cell from forming UDP-galactose (FIG. 3). These two types of galactose insensitive revertants will thus appear as false positive colony forming units on selective plates.

To determine the frequency of reversion to galactose insensitivity, colonies detected on selective plates after mutant frequency determinations were cultured overnight in LB medium in the presence of ampicillin and kanamycin. The frequency of galactose insensitive revertants was determined by replating a small aliquot of mutant cell cultures on agar plates containing 0.21% D-galactose. On a total of 2,246 mutants analyzed, 72 mutants were able to grow in the presence of D-galactose. The total number of transformants was 18,826,745, which would correspond to a reversion frequency of $2.7×10^{-6}$. All revertants analyzed were found to have a dark blue staining on X-gal and a wildtype size pUR288 plasmid.

Galactose insensitive revertants contributed significantly to the overall mutant frequency in E. coli: 38% percent of all mutants analyzed (Table 5). After correction for these revertants, the remaining mutants consisted of 58% no change and 42% size-change mutants, as analyzed by agarose size separation. When restriction patterns of all 16 size-change mutants were analyzed (FIG. 5), only 3 different patterns were obtained, appearing 12 (lane c), 3 (lane d) and 1 (lane e) times, respectively. Rather than assuming that these high-frequency events are mutational hot spots, it is more conceivable that these mutations arose in a relatively early stage of the E. coil growth period of plasmid preparation. After correcting for this "jackpot" effect, the mutant frequency in E. coli is only $0.7×10^{-5}$. Even this figure might be an overestimate, since some of the no change mutants may be due to a clonal effect as well.

Figure 5:
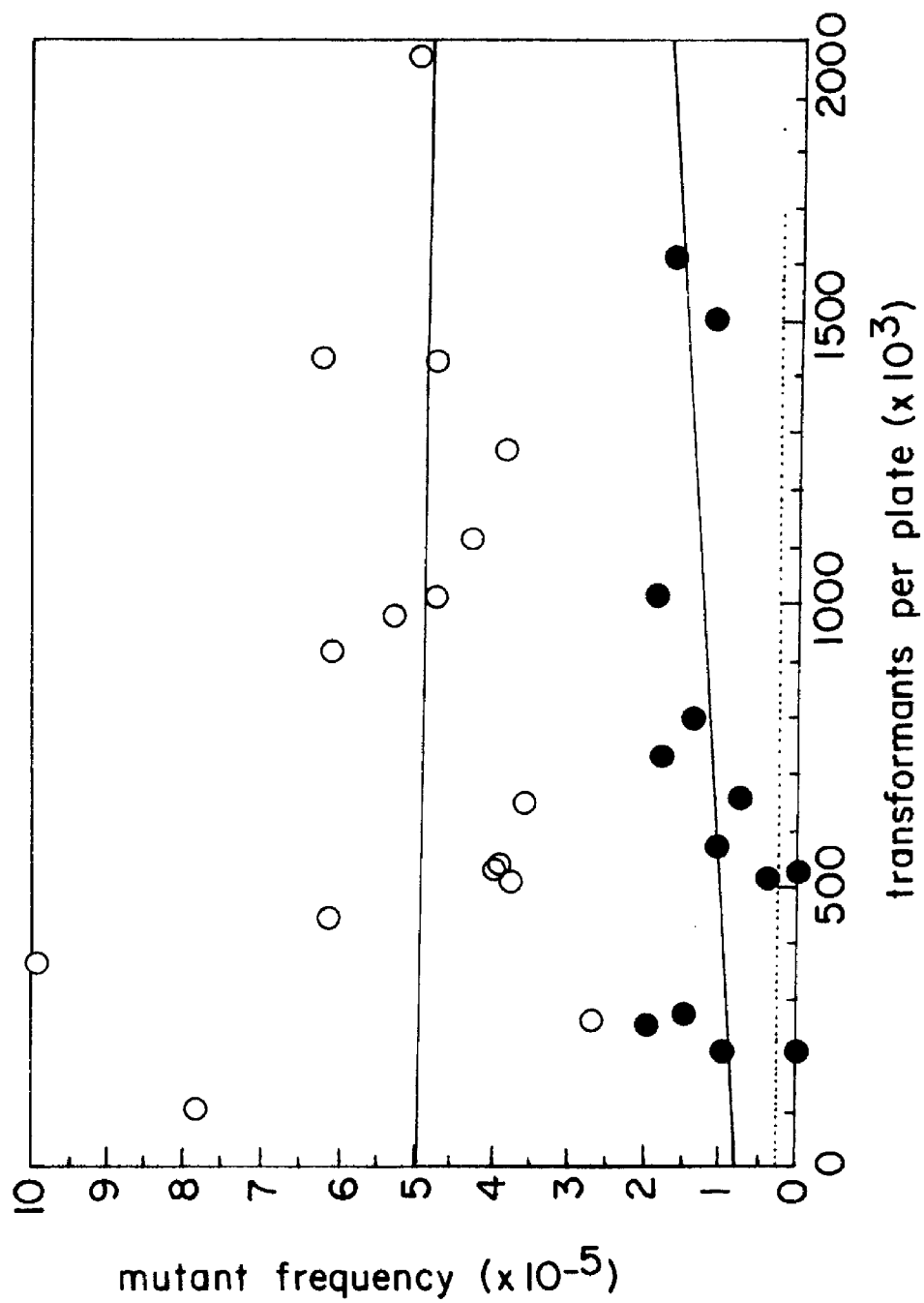
FIG. 5 illustrates the lacZ mutant frequency in mouse and E. coli at different numbers of transformants: (○) Repeated measurements of a liver and a lung genomic DNA sample from untreated animals; (●) Different amounts of isolated pUR288 plasmid electroporated into E. coli C (lacZ$^-$/galE$^-$) cells; (dotted line) Galactose insensitive reversion frequency of E. coli C (lacZ$^-$/galE$^-$).

FIG. 5 graphically displays the contributions of different possible sources to the plasmid mutant spectrum in the mouse. As can been seen, about 20% of the mutants detected in plasmids from the mouse could have originated in *E. coli*, which is not different from the situation in bacteriophage lambda models. However, unlike in lambda models, lacZ mutations in the plasmid system must occur during the first rounds of replication to yield a P-gal resistant phenotype. Indeed, our finding that most of the so-called *E. coli* mutants are the same, indicates that they originated prior to the mutant selection process, during plasmid preparation. The real *E. coli* background is therefore much lower than $1\times10^{-5}$ and possibly closer to $1\times10^{-6}$. In that case the largest source of the non-mouse derived colony forming units on selective plates are the galactose revertants (Table 5).

D. ENU induced mutant frequencies

To demonstrate that the plasmid system is capable of detecting induced mutations, mice were treated intraperitoneally with 100 or 250 mg ENU/kg body weight. The animals were sacrificed at 3, 7 and 14 days after treatment and DNA was extracted from the spleen as described herein. The average mutant frequencies in the spleen at the indicated time points are depicted in FIG. 6. A dose and time dependent increase in mutant frequency was found; up to a 5 fold $[(49\pm9)\times10^{-5}]$ and a 10 fold $[(97\pm19)\times10^{-5}]$ increase for mice treated with 100 mg/kg ENU and 250 mg/kg ENU, respectively, after 14 days as compared to control mice (treated with DMSO only).

E. Characterization of pUR288 mutants obtained from the mouse

Mutant colonies from ENU-treated and untreated mice were examined for β-galactosidase activity on X-gal plates and for DNA size-changes by restriction enzyme analysis on agarose gels. Apparently, part of the mutants had maintained some β-galactosidase activity, as indicated by a blue color with varying intensity on X-gal containing agar plates (Table 6). After growing and re-plating of these individual "color mutants", a uniformly colored population of colonies was obtained excluding the possibility of a mosaic of mutated and non-mutated plasmids. The presence of these color mutants indicates that the system is also capable of detecting mutations in lacZ that only partially inactivate β-galactosidase. The relative number of color mutants increased with the ENU dose (Table 6), possibly because ENU predominantly induces point mutations. Indeed, the ENU-dependent increase of color mutants corresponded with an increased fraction of no-change mutants.

While about 46% of all mutants obtained from the untreated mice were deletions, only about 13% of the mutants induced by 250 mg/kg ENU had undergone size-changes. A selection of size-changed mutants is displayed in FIG. 7A. As ENU is thought to induce predominantly point mutations, these results confirm our expectations. Moreover, all deletion mutants were colorless when grown in the presence of X-gal, while virtually all color mutants had a normal-sized plasmid.

TABLE 6

Spleen mutant characterization after ENU treatment.

| ENU dose time point | Mutants[a] analyzed | β-gal activity white | β-gal activity blue | Mutation type no-change | Mutation type size-change | Inserted mouse sequences |
|---|---|---|---|---|---|---|
| Control | 157 | 70% | 30% | 54% | 46% | 1.9% |
| 100 mg/kg 7 days | 60 | 62% | 38% | 70% | 30% | 1.7% |

TABLE 6-continued

Spleen mutant characterization after ENU treatment.

| ENU dose time point | Mutants[a] analyzed | β-gal activity white | β-gal activity blue | Mutation type no-change | Mutation type size-change | Inserted mouse sequences |
|---|---|---|---|---|---|---|
| 250 mg/kg 7 days | 77 | 40% | 60% | 86% | 14% | 2.6% |
| 250 mg/kg 14 days | 143 | 63% | 37% | 87% | 13% | 1.4% |

[a]Mutants were derived from 2 independent experiments, in each of which 3 animals were used per dose/time point.

In total eight out of 120 deletion mutants were found to have mouse sequences incorporated in the plasmid. These plasmids ranged in size from 2.9 kb to 13 kb (FIG. 7B, lane n, o and p). To rule out the possibility that these mouse sequences were a cloning artifact, plasmids were always redigested with HindIII. The results obtained showed that in all cases HindIII digestion resulted in linearization of the plasmid in only one fragment.

Figure 4:
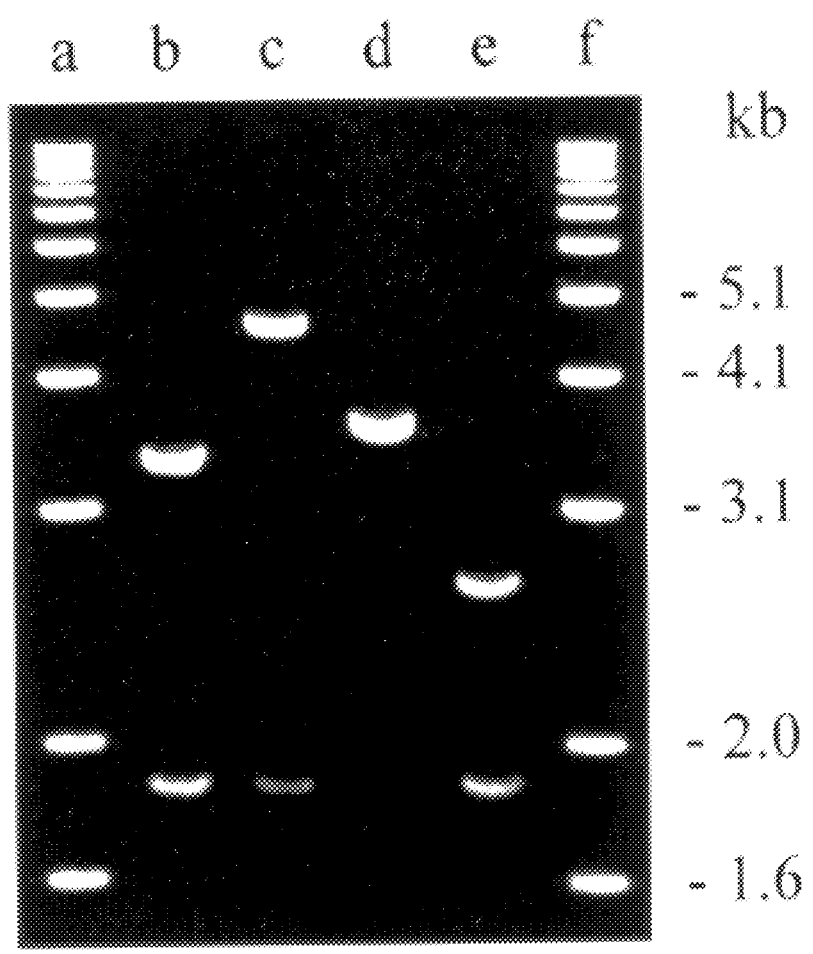
FIG. 4 illustrates the agarose size fractionated, ethidium bromide stained PstI/SacI digested size-change mutant plasmids obtained from E. coli. Lanes are: (a, f) 1 kb DNA ladder (Gibco BRL); (b) no-change mutant; (c, d, e) size-change mutants found 12, 3 and 1 times, respectively.

None of the size-change mutations in the mouse were identical to those found in *E. coli* in the plasmid electroporation experiment described above (compare FIG. 4 with FIG. 7A).

Exemplification

Example 1: Preparation of transgenic animals

About 200 copies of the pUR288 plasmid (Rüther and Müller-Hill (1983) *EMBO J* 2:1791–1794), linearized with the restriction enzyme PstI, were microinjected into fertilized C57B1/6J mouse oocytes. The offspring was analyzed for the presence of the transgene, by means of Southern blot analysis of tail DNA using $^{32}$P-labeled pUR288 as a probe, and crossed into homozygosity. All results mentioned in this study were obtained with transgenic mice of line 60 (C57B1/6#60), harboring about 20 copies per haploid genome.

All animals were bred and maintained in the Beth Israel Hospital Animal Research Facility in accordance with all applicable state and federal regulations in a viral antigen free environment. The room temperature was 23° C. and the light/dark cycle was 12h/12h. Lab chow and water were supplied ad libitum.

For studying spontaneous mutagenesis, female animals of about 4 weeks of age were selected at random and sacrificed by decapitation following asphyxiation. The organs were frozen at −80° C. until used for DNA isolation.

Example 2: ENU treatment

Female mice were treated at 6 weeks of age with a single intraperitoneal (i.p.) injection of 100 mg or 250 mg ethyl nitrosourea (ENU; Sigma) per kg bodyweight. ENU was dissolved in dimethyl sulfoxide (DMSO) to a final concentration of 40 mg/ml immediately before use. Control mice received the vehicle DMSO only. Mice were sacrificed by decapitation following asphyxiation at various time points after the treatment. The control mice were all sacrificed at the latest time point. The organs were frozen at −80° C. until used for DNA isolation.

Example 3: Genomic DNA isolation (i) phenol-chloroform

Organ tissues were rapidly homogenized in 9 ml lysis buffer (10 mM Tris-HCl, pH 8.0; 150 mM NaCl; 100 mM EDTA) in a 50 ml Falcon tube using a Brinkmann homogenizer. SDS, proteinase K (Boehringer), RNase $T_1$ and RNase A (Boehringer) were added to final concentrations of 1%, 0.5 mg/ml, 120 µg/ml and 120 µg/ml, respectively. The mixture was incubated for 3 hours at 55° C. while rotating and subsequently extracted with 1 volume phenol:chloroform:isoamyl alcohol (25:24:1) by gently mixing the emulsion for 10 minutes. The two phases were separated by centrifugation for 20 minutes at 4,000 -g after which the aqueous phase was transferred to a clean 50 ml Falcon tube. One fifth volume of 8 M potassium acetate was added to the aqueous phase. The mixture was extracted with 1 volume chloroform by gently mixing the emulsion for 10 minutes. The two phases were separated by centrifugation for 20 minutes at 4,000 xg after which the aqueous phase was transferred to a clean 50 ml Falcon tube. Two volumes of pure ethanol were added to the aqueous phase. The precipitated genomic DNA was spooled on a glass pipette and washed 3 times with 1 ml 70% ethanol. After the excess of ethanol was removed, the DNA pellet was air-dried for 10 minutes and solubilized in 0.5 to 1 ml TE-buffer (10 mM Tris-HCl, pH 7.5; 1 mM EDTA). DNA concentrations were determined by spectrophotometric measurements at $OD_{260}$.

(ii) Qiagen kit

For rapid DNA extraction the "Qiagen Tissue Kit" (method 2 in Table 3) was used. All buffers used were provided with the kit. Organ and tissue homogenate was digested in 20 ml buffer G2 containing 20 mg/ml Proteinase K (Proteinase K (Gibco BRL) and 200 µg/ml RNase A (Boehringer Mannheim) for two hours at 50° C. After vortexing for 10 seconds, the mixture was applied to a "Qiagen Genomic-tip 500/G", equilibrated with 10 ml buffer QBT. The column was washed twice with 15 ml buffer QC and the DNA was eluted with 15 ml buffer QF. After addition of 10.5 ml isopropanol to the elute, the DNA was spooled with a glass transfer pipette, washed with 70% ethanol, air dried for ten minutes and redissolved in 0.3 ml TE. DNA concentrations were determined spectrophotometrically at 260 mm.

Example 4: Preparation of electrocompetent cells

One and a half ml of an overnight culture of *E. coli* C (lacZ$^-$/galE$^-$), grown in LB-medium (Gibco BRL) containing 25 µ/ml kanamycin (Sigma), was added to 500 ml LB-medium in a 1 liter Erlenmeyer flask. The cell culture was grown at 37° C. while shaking at 225 rpm. to $OD_{600}$=0.45 and subsequently placed on ice for minutes while shaking. The cell culture was aliquoted in 50 ml Falcon tubes and centrifuged at 4° C. for 15 minutes at 4000 xg and washed once with 0.5 volume ice-cold dd$H_2O$, once with 0.25 volume ice-cold dd$H_2O$ and once with 0.1 volume ice-cold 10% glycerol. During the wash steps, cells were carefully resuspended by gently inverting the tubes. Finally, the cells were resuspended in ice-cold 10% glycerol to $OD_{600}$=57. Aliquots of 250 µl were frozen in a dry-ice/ethanol bath nd stored at -80° C.

Example 5: Plasmid rescue

One ml of M450 magnetic beads coated with sheep anti-mouse IgG (4 ×10$^8$ magnetic beads/ml; Dynal) were pelleted on a magnetic particle concentrator (Dynal) and washed once with 1 ml PBS (pH 7.4). The beads were resuspended in 850 µl PBS and 150 µl mouse anti-β-galactosidase (2 mg/ml; Promega) was added. The mixture was incubated for 1 hour at 37° C. in a rotating incubator. The beads were washed 3 times with 1 ml PBS. After the last wash step the beads were resuspended in 900 µl PBS and 100 µl of a lacZ/lacI fusion protein, kindly provided by Dynal (Oslo, Norway). The mixture was incubated for 2 hours at 37° C. in a rotating incubator. The beads were washed 3 times with 1 ml PBS. Finally, the beads were resuspended in 1 ml PBS and stored at 4° C. for a maximum of four months.

One to 50 µg of transgenic mouse DNA was diluted to a 58 µl volume with dd$H_2O$. Fifteen µl 5× binding buffer (50 mM Tris-HCl, pH 7.5; 5 mM EDTA; 50 mM MgCl$_2$; 25% glycerol; adjusted to pH 6.8 with HCl) and 2 µl Hind III (20 U/µl; New England BioLabs) were added. Sixty µl of magnetic beads coated with the lacZ/lacI fusion protein were pelleted on a magnetic particle concentrator and the supernatant was removed. The pre-coated beads were resuspended in the genomic DNA/HindIII/binding buffer mixture and incubated for 60 minutes at 37° C. while rotating. The beads were pelleted, washed once with 250 µl 1× binding buffer and resuspended in 75 µl IPTG-elution buffer (10 mM Tris-HCl, pH 7.5; 1 mM EDTA; 125 mM NaCl) and 5 µl of 25 mg/ml isopropylthio-β-galactoside (IPTG; Promega). One hundred µl dd$H_2O$, 20 µl×NEBuffer #2 (New England BioLabs) and 1 µl 20 U/µl Hind III were added to the resuspended beads, mixed and incubated at 37° C. for 30 minutes while rotating. The mixture was subsequently placed in a 65° C. waterbath for 20 minutes in order to inactivate the HindIII. The mixture was allowed to cool to room temperature before 2 µl of a 10 mM ATP stock (Boehringer) and 1 µl of a 10× dilution of 1 U/µl T4 DNA ligase in 1×T4 DNA ligase buffer (Gibco BRL) were added. After a 1 hour ligation at room temperature the supernatant was separated from the beads. The beads were discarded and DNA was precipitated by adding 30 µl glycogen (20 µg/82 l) (Boehringer), 0.1 volume 3 M sodium acetate, pH 4.9, and 2.5 volumes 95% ethanol. After 1 hour at -80° C., DNA was pelleted by centrifugation for 30 minutes at 14,000 rpm in a microcentrifuge. The pellet was washed once with 250 µl 70% ethanol. All ethanol was removed by aspiration and the pellet was air-dried for 10 minutes. The DNA was finally resuspended in 5 µl dd$H_2O$.

Electroporations were performed by adding 60 µl ice-cold electrocompetent *E. coli* C (lacZ$^-$/galE$^-$) cells directly to the resuspended DNA. The mixture was placed on a magnetic particle concentrator, before it was transferred to ice-cold electroporation cuvettes, to avoid any carry-over of remaining beads. Electroporation conditions were 25 µF and 1.8 kV for the Gene Pulser apparatus and 200 Ω for the Pulse Controller using 0.1 -cm cuvettes (Biorad). After electroporation, 1 ml ice-cold SOB medium (2% Bacto tryptone; 0.5% Bacto yeast extract; 0.05% NaCl; 2.5 mM KCl; 5 mM MgCl$_2$, adjusted to pH 7.0 with 5 N NaOH) was added to the cells immediately. The cells were then transferred to a 15 ml culture tube, containing an additional 1 ml of SOB medium, and incubated in a shaking incubator for 30 minutes at 37° C. and 225 rpm. Two µl (0.1%) of the cell culture was diluted in 2 ml SOB medium and plated with 13 ml agar (6.125 g/l LB Broth Base (Gibco BRL); 6.125 g/l Antibiotic Medium 2 (Difco), containing 75 µg/ml ampicillin (Sigma), 25 µg/ml kanamycin (Sigma), 75 µg/ml 5-bromo-4-chloro-3-indolyl-β-D-galactoside (X-gal; Promega) and 75 ng/ml 2,3,5-triphenyl-2H-tetrazolium chloride (Aldrich), to determine the rescue efficiency. The remainder of the cell culture was plated with 13 ml agar, containing 75 µg/ml ampicillin, 25 µg/ml kanamycin, 0.3% phenyl-β-D-galactoside (P-gal; Sigma) and 75 ng/ml 2,3,5- triphenyl-2H-tetrazolium chloride, to select those cells harboring mutant plasmids. Mutant frequencies were determined as the ratio between the number of colonies on selective (P-gal) plates versus the number of colonies on non-selective plates times the dilution factor (1000×).

Example 6: Southern blot hybridization analysis

DNA samples were size-fractionated on a 1% agarose TBE (90 mM Tris-borate; 4 mM EDTA, pH 8.0) gel and subsequently alkaline-transferred to a Hybond-N[30] nylon membrane (Amersham). Wild type pUR288 plasmid was $^{32}$P-labeled by the random prime method (high prime DNA labeling mix; Boehringer). The blot was hybridized with the pUR288 probe overnight at 65° C. in 15 ml hybridization buffer (0.5 M sodium phosphate, pH 7.2; 7% SDS) and subsequently washed 2 times for 30 minutes at 65° C. with 2.5×SSC (375 mM NaCl; 37.5 mM sodium citrate, pH 7.0), 0.1% SDS and 2 times for 30 minutes at 65° C. with 2.5×SSC only. Radioactive signals on blot were visualized by exposing X-Omat AR films (Kodak) and quantified by PhosphorImager analysis (Molecular Dynamics).

Example 7: Bacterial plasmid preparation and electroporation

E. coli cells harboring the wild-type pUR288 plasmid were obtained in the form of a dark blue staining colony on a titer plate from a regular mutant frequency determination. These cells were grown in 3 ml LB medium containing 75 µg/ml ampicillin and 25 µg/ml kanamycin for 8 hours at 37° C., 225 rpm. Cells were harvested by centrifugation for 10 minutes at 1000 ×g. The cell pellet was resuspended in 400 µl lysis buffer and transferred to microcentrifuge tubes. The DNA isolation procedure was continued as described above for genomic DNA isolations. Finally the DNA pellet was solubilized in 50 µl TE-buffer (10 mM Tris-HCl, pH 7.5; 1 mM EDTA). One to 5 µl of a dilution in ddH$_2$O was mixed with 60 µl of electro-competent E. coli C (lacZ[31] /galE[31] ) cells. Transformation and plating of the cells was performed as is described above for the plasmid rescue procedure.

Example 8: Characterization of mutant plasmids

Mutant colonies were transferred from the selective plates to Falcon culture tubes containing 3 ml LB-medium, 25 µg/ml kanamycin and 75 µg/ml ampicillin and grown overnight at 37° C. and 225 rpm. One µl of each cell culture was pipetted onto LB-agar plates containing 75 µg/ml ampicillin, 25 µg/ml kanamycin and either 0.21 % D-galactose (Sigma) or 75 µg/ml X-gal. After overnight incubation at 37° C., colonies were analyzed for growth on D-galactose (for galactose (in)sensitivity), and color on X-gal (for β-galactosidase activity).

Minipreps were isolated from the 3 ml cell cultures using the Insta-Mini-Prep-kit (5 prime–3 prime, Boulder, Colo., U.S.A.). Miniprepped plasmids were digested with PstI and SacI (New England BioLabs), and subjected to Southern blot hybridization analysis using genomic (non transgenic) mouse DNA as a probe.

Example 9: Influence of pH on plasmid rescue

In this experiment the pH of the binding buffer was varied. The binding buffer was the only buffer present. Therefore, no Hind III restriction enzyme buffer (Neb#2) was added. The Mg++ end concentration was 20 mM. It is clear that the best results were obtained, not at pH 7.6, but at pH 6.7. The efficiency of binding was determined from hybridization experiments, as shown in FIG. 3. That is, the intensity of the plasmid band, obtained before and after magnetic rescue, was measured. The results are shown in Table 7.

TABLE 7

Influence of binding buffer pH on rescue of pUR288 plasmids

| | pH | | | |
|---|---|---|---|---|
| | 6.7 | 7.2 | 7.7 | 7.9 |
| Experiment 1 | 95 | 93 | 83 | 64 |
| Experiment 2 | 92 | 81 | nd | nd |

Example 10: Influence of Mg++ concentration on rescue efficiency

In this experiment the whole process of rescue was performed (including magnetic separation, ligation and electrotransformation) at the optimal pH of 6.7, and at two concentrations of Mg++. Mg++ is essential for the binding to occur (without it there is no binding). In the original rescue protocol it was never added. However, its importance was not understood because it was present in the Neb#2 buffer, the digestion buffer. The yield was determined at two Mg++ end concentrations: 20 mM and 10 mM. For a number of different DNA samples the yields are clearly better at a concentration of 10 mM. Therefore, it can be concluded that although Mg++ should be present, its concentration cannot be too high. The results are shown in Table 8.

TABLE 8

Influence of MgCl$_2$ concentration on rescue efficiency

| | Number of transformants | |
|---|---|---|
| Sample ID | [100]$^a$ | [50]$^a$ |
| MD1 | 764,000 | 2,028,000 |
| LU-CONT1 | 76,000 | 384,000 |
| LU-CONT3 | 260,000 | 1,272,000 |
| LU1-3d | 136,000 | 708,000 |
| LU1-14d | 115,000 | 488,000 |

$^a$Concentration of MgCl$_2$ in 5X binding buffer (mM). The final [MgCl$_2$] was 20 and 10 mM, respectively. The pH of 5X binding buffer was 6.7.

From results in Tables 6 and 7 it can be concluded that pH 6.7 is optimal for the binding and 10 mM Mg++ is optimal for both binding and the plasmid rescue.

Example 11: Simultaneous versus consecutive restriction enzyme digestion and plasmid binding In this experiment simultaneous Hind III digestion and magnetic bead binding to the plasmid-containing mouse chromosomal DNA was compared to consecutive Hind III digestion and binding as in the original protocol. Clearly, simultaneous digestion and binding in the binding buffer (no Neb#2 present) yielded much better results, both in terms of the number of plasmids rescued (the number of transformants) and in terms of binding (determined by hybridization analysis). The results are shown in Table 9.

Two factors play a role here. First, the Neb#2 Hind III buffer negatively influences the binding. This buffer is provided by the manufacturer to perform the Hind III digestion. Second, the kinetics of the binding of magnetic beads (coated with the lacZ/lacI fusion protein) is much better with large DNA fragments.

TABLE 9

Simultaneous versus consecutive restriction enzyme digestion and plasmid binding

| Sample ID | Binding | MgCl$_2$ (mM) | Number of transformants |
|---|---|---|---|
| MD1 (con) | − | 50 | 680,000 |
| MD1 (sim) | + | 50 | 2,028,000 |
| MD1 (sim) | + | 100 | 764,000 |

Example 12: Influence of ATP concentration on rescue efficiency

After magnetic bead separation, ligation and ethanol-precipitation. it was observed that the size of the pellet (DNA with salts) influenced the efficiency of transformation; a large pellet had a low efficiency and a small pellet a high efficiency. After extensive investigations it was found that the high concentration of ATP was the cause of the large pellet. ATP is necessary for the ligation, but after reducing the ATP end concentration from 10 mM (concentration in the original protocol) to 1 mM, the pellet was found to be much smaller and the rescue efficiencies much higher. The results are shown in Table 10.

TABLE 10

Influence of ATP concentration on rescue efficiency

| | Number of transformants | |
|---|---|---|
| Sample # | [1]$^a$ | [0.1]$^a$ |
| Scont3 | 61,000 | 569,000 |
| S250 3.1 | 10,000 | 784,000 |
| S250 7.1 | 6,000 | 191,000 |
| S250 7.2 | 3,000 | 454,000 |
| S250 14.1 | 53,000 | 1,084,000 |
| S250 14.2 | 0 | 590,000 |

$^a$Concentration of ATP during ligation (mM).

All of the above cited references and publications are hereby incorporated by reference.

Other embodiments are within the following claims.

What is claimed is:

1. A method of testing for mutagenesis, comprising:
   providing an organism or a cell which includes a plasmid vector comprising a nucleic acid test region which is integrated into DNA of said organism or said cell, wherein said test region comprises a binding region which specifically binds to a capture moiety;
   exposing said organism or said cell to a treatment;
   recovering said vector by excising said vector from said DNA and contacting said vector with said capture moiety, wherein said excising step and said contacting step are performed simultaneously in a reaction mixture or wherein said contacting step is performed prior to said excising step; and
   determining the presence of a mutation in said test region.

2. The method of claim 1, further comprising a ligation step wherein said test region is circularized.

3. The method of claim 1, wherein the presence of said mutation is determined through a positive selection procedure.

4. The method of claim 1, wherein said test region further comprises, in addition to a binding region, a marker gene.

5. The method of claim 4, wherein said binding region comprises a lac operator sequence.

6. The method of claim 4, wherein said marker gene is a LacZ gene.

7. The method of claim 1, wherein said test region is a pUR288 plasmid.

8. The method of claim 1, wherein said capture moiety comprises a magnetic bead coupled to a LacI fusion protein.

9. The method of claim 8, wherein said LacI fusion protein is selected from the group consisting of a LacZ/LacI fusion protein and a ProteinA/LacI fusion protein.

10. The method of claim 1, wherein said reaction mixture comprises a binding buffer which promotes the binding of said test region to said capture moiety.

11. The method of claim 10, wherein said binding buffer comprises Mg++ in the range of about 6 to about 12 mM.

12. The method of claim 10, wherein said binding buffer has a pH range of about 6.5 to about 7.5.

13. The method of claim 1, wherein said treatment includes exposing said organism or said cell to an agent.

14. The method of claim 13, wherein said agent is selected from a group consisting of radiation, synthetic chemicals or natural compounds.

15. A method of testing for mutagenesis, comprising:
   providing an organism or a cell which includes a vector integrated into DNA of said organism or said cell, said vector comprising a binding region which specifically binds to a capture moiety, and a marker gene the function of which can be altered by a mutation;
   exposing said organism or said cell to a treatment;
   excising said vector from said DNA in the presence of said capture moiety, wherein said excising step and a contacting step are performed simultaneously in a reaction mixture or wherein said contacting step is performed prior to said excising step, such that said excised vector is bound to said capture moiety;
   recovering said excised vector from said capture moiety;
   transforming a host cell with said vector; and
   determining the presence of a mutation in said marker gene by testing for an altered function of said marker gene.

16. A method of testing for mutagenesis, comprising:
   providing an organism or a cell which includes a vector integrated into DNA of said organism or said cell, said vector comprising a test region, wherein said test region includes a binding region which specifically binds to a capture moiety;
   exposing said organism or said cell to a treatment;
   recovering said vector by excising said vector from said DNA and contacting said vector with said capture moiety,
   ligating said vector in the presence of ATP in the range of about 0.05 mM to about 0.2 mM, wherein co-precipitation of ATP with said vector is minimized; and determining the presence of a mutation in said test region.

17. A method of testing for mutagenesis, comprising:
   providing an organism or a cell which includes a vector integrated into DNA of said organism, said vector comprising a lac operator sequence and a LacZ marker gene;
   exposing said organism or said cell to a treatment;
   excising said vector from said DNA in the presence of a capture moiety, wherein said capture moiety comprises a LacZ/LacI fusion protein coupled to a magnetic bead, and wherein said excising step and a contacting step are performed simultaneously in a reaction mixture or wherein said contacting step is performed prior to said excising step, such that said excised vector is bound to said capture moiety;

recovering said excised vector from said capture moiety;

transforming a host cell with said vector;

ligating said vector in the presence of ATP in the range of about 0.05 mM to about 0.2 mM, wherein co-precipitation of ATP with said vector is minimized; and determining the presence of a mutation in said LacZ marker gene by testing for an altered function of said marker gene.

18. A kit for mutagenesis testing comprising:

a nucleic acid test region capable of integration into the DNA of a cell or an organism, wherein said test region comprises a binding region capable of specific binding to a capture moiety;

a capture moiety; and a binding/excision buffer which allows for excision of said test region from said DNA and a binding of said test region to said capture moiety to occur simultaneously.

19. A kit of claim 18, further comprising a restriction endonuclease.

20. A kit of claim 18, further comprising a ligation buffer for circularization of said test region.

21. A kit of claim 20, wherein said ligation buffer comprises ATP in the range of about 0.05 mM to about 0.2 mM.

22. A kit of claim 18, further comprising a host cell.

23. A kit of claim 18, wherein said test region further comprises, in addition to a binding region, a marker gene.

24. A kit of claim 18, wherein said binding/excision buffer comprises Mg++ in the range of about 6 to about 12 mM.

25. A kit of claim 18, wherein said binding buffer has a pH range of about 6.5 to about 7.5.

26. A kit of claim 18, wherein said test region is a pUR288 plasmid.

27. A kit of claim 18, wherein said capture moiety is a LacI fusion protein coupled to a magnetic bead.

28. A kit of claim 27, wherein said LacI fusion protein is selected from the group consisting of a LacI/LacZ fusion protein and a LacI/ProteinA fusion protein.

* * * * *